US00PP15452P2

(12) United States Plant Patent
Hirose

(10) Patent No.: US PP15,452 P2
(45) Date of Patent: Dec. 21, 2004

(54) ***PIERIS* PLANT NAMED 'KATSURA'**

(50) Latin Name: *Pieris japonica*
Varietal Denomination: Katsura

(76) Inventor: Yoshimichi Hirose, Y. Hirose, 3-20-14 Yamate-cho, Iwakuni, Yamate-Chou (JP), 740-0022

( * ) Notice: Subject to any disclaimer, the term of this patent is extended or adjusted under 35 U.S.C. 154(b) by 0 days.

(21) Appl. No.: 10/300,106

(22) Filed: Nov. 20, 2002

(51) Int. Cl.[7] ..... A01H 5/00
(52) U.S. Cl. ..... Plt./226
(58) Field of Search ..... Plt./226

(56) References Cited

U.S. PATENT DOCUMENTS

PP4,111 P * 9/1977 Zebehazy ..... Plt./226
PP4,794 P * 11/1981 Verkade ..... Plt./226
PP7,872 P * 5/1992 Belgiorno ..... Plt./226

OTHER PUBLICATIONS http://www.esveld.nl/engels.htm.* http://www.esveld.nl/dialijsten/dialistgPieris.html.*

UPOV ROM GTITM Computer Database, GTI Jouve Retrieval Software 2003/03 Citation(s) for 'Katsura'.*

* cited by examiner

*Primary Examiner*—Kent Bell
*Assistant Examiner*—W C Haas

(57) ABSTRACT

A new cultivar of *Pieris* named 'Katsura' that is distinguished by a broad, bushy habit, wine-red leaves that later turn green and rose-colored flowers in spring. In combination these traits set 'Katsura' apart from all other existing varieties of *Pieris* known to the inventors.

3 Drawing Sheets

Genus: *Pieris.*
Species: *japonica.*
Demonination: Katsura.

BACKGROUND OF THE INVENTION

The present invention relates to a new and distinct cultivar of lily-of-the-valley shrub and is a perennial that is grown for use as an ornamental landscape and container plant. The new invention is known botanically as *Pieris japonica* and will be referred to hereinafter by the cultivar name 'Katsura'.

'Katsura' was discovered by the inventor in 1986 in a cultivated area of Kazakai, Hirata, Japan as a sport of the parent plant *Pieris japonica* (unpatented). The inventor is a collector of plants and author of numerous books on the subject of variegated plants, and observed the unique qualities of 'Katsura'. The inventor selected 'Katsura' for its dark red new foliage, and rose-colored flowers. The wine-red foliage turns dark green.

The distinguishing characteristics of 'Katsura' are, continuous new growth through spring and summer, large glossy leaves that are wine-red in color before turning green, and rose-colored flowers. For best performance 'Katsura' requires semi-shade or sun, and slightly acidic soil with a ph of 4.5 to 5.5.

The closest comparison plant is *Pieris japonica* 'Red Mill' (not patented). 'Katsura' is distinguishable from 'Red Mill' by flower color, dark red new growth, and large glossy leaves.

The first asexual reproduction of 'Katsura' was carried out by the inventor in 1989 in order to provide a plant for evaluation and further multiplication at the nursery firm Fa. C. Esveld in Boskoop, The Netherlands. The method used was softwood cuttings. Since that time subsequent generations have been determined stable and true to type.

SUMMARY OF THE INVENTION

The following traits have been repeatedly observed and represent the distinguishing characteristics of the new *Pieris* cultivar. These traits in combination distinguish 'Katsura' from all other existing varieties of *Pieris* known to the inventors. 'Katsura' has not been tested under all possible conditions and phenotypic differences may be observed with variations in environmental, climatic, and cultural conditions, however, without any variance in genotype.

1. *Pieris* 'Katsura' exhibits a broad, upright, bushy habit.
2. *Pieris* 'Katsura' exhibits rose-colored flowers and glossy leaves.
3. *Pieris* 'Katsura' exhibits new foliage that is wine-red in color and later changes to dark green.
4. *Pieris* 'Katsura' blooms in early spring.
5. *Pieris* 'Katsura' reaches 300 cm. in height and 150 cm. in width at maturity.
6. *Pieris* 'Katsura' is an evergreen shrub.
7. *Pieris* 'Katsura' is hardy to USDA Zone 6.

BRIEF DESCRIPTION OF THE DRAWINGS

The accompanying drawings illustrate the overall appearance of the new *Pieris* cultivar 'Katsura' showing the colors as true as it is reasonably possible to obtain in colored reproductions of this type. Colors in the drawings may differ from the color values cited in the detailed botanical description, which more accurately describes the actual colors of the new variety 'Katsura'. The drawings were made in spring and fall of 2001 of two and one half year old plants, and three year old plants grown out-of-doors in a cultivated area of Boskoop, The Netherlands.

The first drawing is a close-up of the flowers.

The second drawing illustrates the new wine-red foliage before it turns green.

The third drawing illustrates the plant from a side perspective in bloom and exhibiting green foliage.

Drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new *Pieris* cultivar 'Katsura'. Observations, measurements, values and comparisons were compiled in Arroyo Grande Calif. from two and a half year old plants and three year old plants grown out-of-doors. Color determinations are made in accordance with the 2001 The Royal Horticultural Society Colour Chart from London England, except where general color terms of ordinary dictionary significance are used.

Botanical classification: *Pieris* 'Katsura'.
Species: *japonica.*
Common name: Lily-of-the-valley shrub.
Parentage: *Pieris* 'Katsura' is a sport of the parent plant *Pieris japonica.*
Propagation method: Softwood cuttings.
Rooting habit: Fine and fibrous.
Time to develop roots: 6–8 weeks are needed for the initial cuttings to develop roots.
Temperature to develop roots: 15–20° Centigrade air temperature.
Crop time: 30 months are needed to produce a finished product from a rooted cutting.
Growth habit: Broad, upright and bushy habit.
Plant shape: Globular to flattened globular.
Vigor: Low.
Suggested container size: 17 cm. container.
Use: Ornamental landscape plant or container plant.
Type: Perennial.
Height of mature plant: Approximately 300 cm. in height at maturity.
Width of mature plant: Approximately 150 cm. in width at maturity.
Cultural requirements: Plant in semi-shade or sun with slightly acidic soil that has a ph of 4.5–5.5.
Diseases and pests: Susceptible to Phytophthora.
Hardiness: USDA Zone 6.
Stem:
- *Branching habit.*—Freely branching. Main shoots appear from base.
- *Stem colors.*—The colors of young stems range are a combination of RHS 176A and 178A and the colors of mature stems are a combination of RHS 143B and 177A.
- *Stem shape.*—Cylindrical.
- *Stem surface.*—The surface of stems is mostly glabrous but with slight lengthwise ribbing.
- *Stem strength.*—Moderate.
- *Lateral branches.*—The average number of lateral branches is 18.
- *Lateral branch length.*—Average length is 5.7 cm.
- *Lateral branch diameter.*—Average diameter is 2 mm.
- *Internode length.*—Average internode length is 3 mm.
- *Pubescence.*—Absent.

Foliage:
- *Type.*—Evergreen.
- *Leaf arrangement.*—Alternate.
- *Single or compound.*—Single.
- *Leaf division.*—Simple.
- *Quantity of leaves per lateral branch.*—Average of 13.
- *Leaf shape.*—Oblanceolate to narrow elliptic.
- *Leaf length.*—An average of 4.9 cm. in length.
- *Leaf width.*—An average of 1.4 cm. in width.
- *Leaf base.*—Attenuate.
- *Leaf apex.*—Acute.
- *Leaf venation pattern.*—Anastomosing.
- *Vein color.*—On upper surface veins are 144A and on lower surface veins veins are 144C.
- *Margin.*—Upper half serrate.
- *Leaf surface* (*abaxial surface*).—Slightly rugose.
- *Leaf surface* (*adaxial surface*).—Slightly rugose.
- *Pubescence.*—Absent.
- *Leaf attachment.*—Petiolate.
- *Petiole dimensions.*—9 mm. in length and 1 mm. in diameter.
- *Petiole color.*—144A on upper surface exposed to the sun, and 144C on the under surface.
- *Durability of foliage to stress.*—Moderate.
- *Presence of stipules or spines.*—None.
- *Mature leaf color* (*adaxial surface*).—Closest to 137A but darker.
- *Mature leaf color* (*abaxial surface*).—143A.
- *Young leaf color* (*adaxial surface*).—Closest to 183A but more reddish.
- *Young leaf color* (*abaxial surface*).—176A.

Flower:
- *Inflorescence.*—Raceme.
- *Flower arrangement.*—Terminal raceme.
- *Aspect: Drooping.*
- *Dimensions of inflorescence.*—2.3 cm. in width and 5 cm. in height.
- *Quantity of flowers per inflorescence.*—An average of 22.
- *Flower type or form.*—Single.
- *Flowering habit.*—Blooms once a year.
- *Quantity of flowers per lateral stem.*—Average of 88.
- *Quantity of flowers and buds per plant.*—Average of 1575.
- *Natural flowering season.*—Early spring.
- *Flower response time.*—Approximately 11 months.
- *Peduncle dimensions.*—5 mm in length and 1.20 mm. in width.
- *Peduncle angle.*—0–80°.
- *Peduncle color.*—166A.
- *Peduncle strength.*—Moderate.
- *Margins.*—Entire.
- *Flower fragrance.*—Moderately sweet.
- *Bud shape.*—Ovate.
- *Bud dimensions.*—2 mm. in diameter and 3 mm. in length.
- *Bud color.*—N186C.
- *Rate of opening.*—All flowers are open approximately 7 days after the first flowers have opened.
- *Flower shape.*—Urceolate.
- *Flower dimensions.*—7 mm. in diameter and 9 mm. in height.
- *Flower longevity.*—Lasts over 2 weeks.
- *Self-cleaning or persistent.*—Self-cleaning.

*Petal appearance*.—Dull and slightly ribbed lengthwise with tips of petals reflexed.
*Petal texture*.—Glabrous.
*Petal arrangement*.—Rotate.
*Number of petals*.—Five in number.
*Fused or unfused*.—Fused with the exception of the reflexed tips.
*Petal shape*.—Ovate.
*Petal apex*.—Obtuse.
*Petal dimensions*.—8.5 mm. in length and 5 mm. in width.
*Petal color* (*upper and lower surfaces when opening*) .—A combination of 155C and 186B.
*Petal color on upper surface* (*when fully opened*).—A combination of 155C and 186D.
*Petal color on under surface* (*when fully opened*).—A combination of 155C and 186C.
*Petaloids*.—Absent.
*Sepal appearance*.—Dull and glabrous.
*Sepal arrangement*.—Rotate.
*Number of sepals*.—Five in number.
*Sepal shape*.—Ovate.
*Sepal margin*.—Entire.
*Sepal apex*.—Acute.
*Sepal base*.—Broad cuneate.
*Sepal dimensions*.—3.5 mm. in length and 1.5 mm. in width.
*Sepal color* (*immature under side*).—185A.
*Sepal color* (*immature upper side*).—183C.
*Sepal color* (*mature upper side*).—181A.
*Sepal color* (*mature under side*).—181A.
*Calyx shape*.—Rotate.
*Calyx dimensions*.—1 mm. in length and 7 mm. in diameter.
*Pedicels*.—Present.
*Pedicel dimensions*.—8 mm. in length and 0.75 mm in diameter.
*Pedicel angle*.—10° to 50°.
*Pedicel strength*.—Moderate.
*Pedicel color*.—181A.

Reproductive organs:
*Stamen number*.—Ten.
*Stamens*.—One on a pedicel.
*Anther dimensions*.—1 mm. in height and 1 mm. in length.
*Anther color*.—175B.
*Anther shape*.—Broadly oval and dorsifixed.
*Anther dimensions*.—0.50 mm. in width and 0.50 mm. in length.
*Amount of pollen*.—Low.
*Pollen color*.—N167C.
*Pistil*.—One.
*Pistil length*.—6 mm. in length.
*Ovary color*.—137D.
*Style color*.—154C.
*Style length*.—6 mm. in length.
*Stigma shape*.—Narrow and club-shaped.
*Stigma color*.—187A.

Fruit:
*Number of days to ripening of fruit*.—Average of 40 days.
*Fruit texture*.—Glabrous and dull.
*Fruit color*.—199C.
*Fruit dimensions*.—Average dimensions are 6 mm. in diameter and 5 mm. in length.
*Quantity of fruit per plant*.—An average of 200.
*Quantity of fruit per branch*.—An average of 10.
*Seed color*.—199B.
*Seed dimensions*.—Less than 0.1 mm. in length and less than 0.1 mm. in diameter.
*Quantity of seeds*.—Approximately 250 seeds.

It is claimed:

1. A new and distinct cultivar of *Pieris* plant named 'Katsura' as described and illustrated.

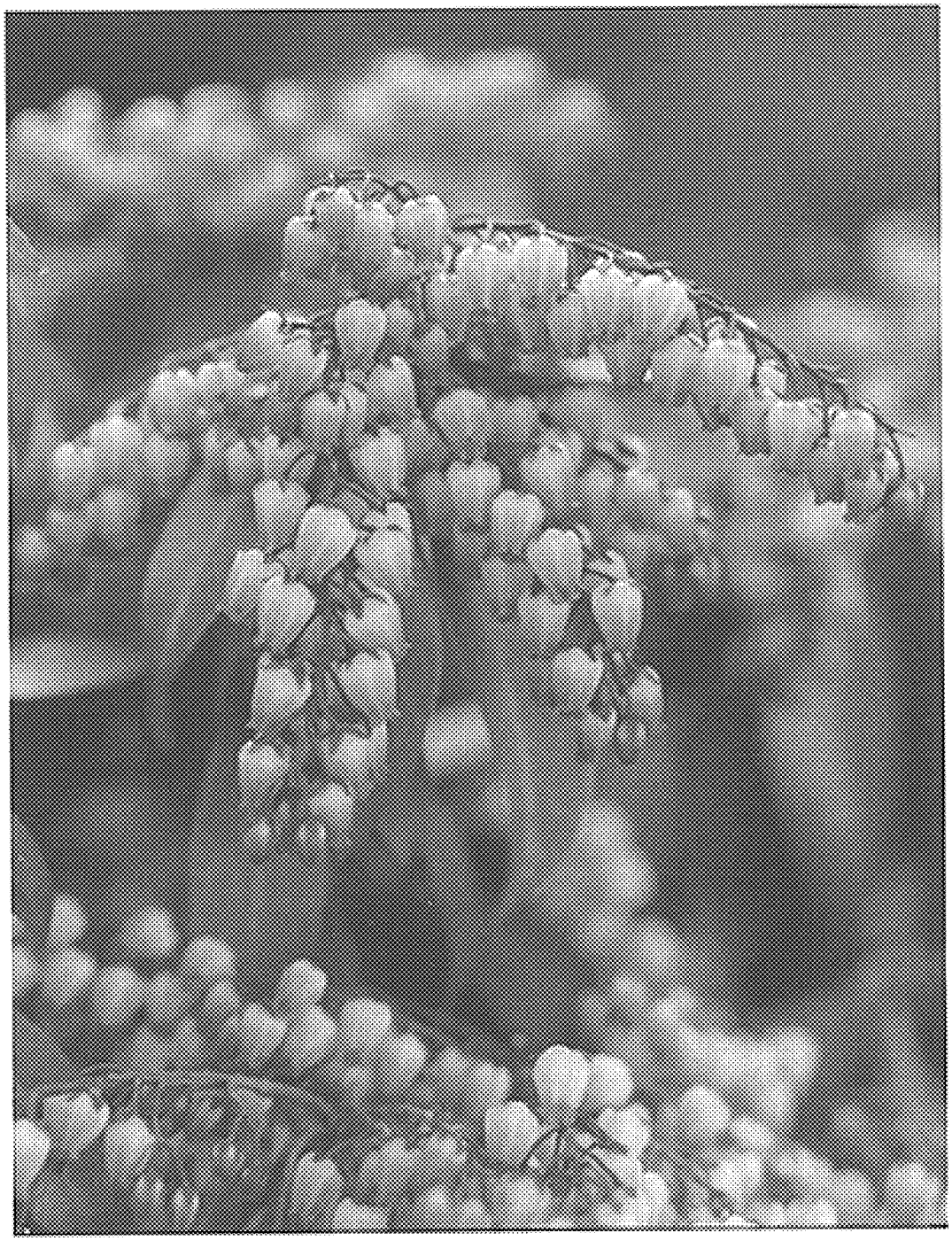

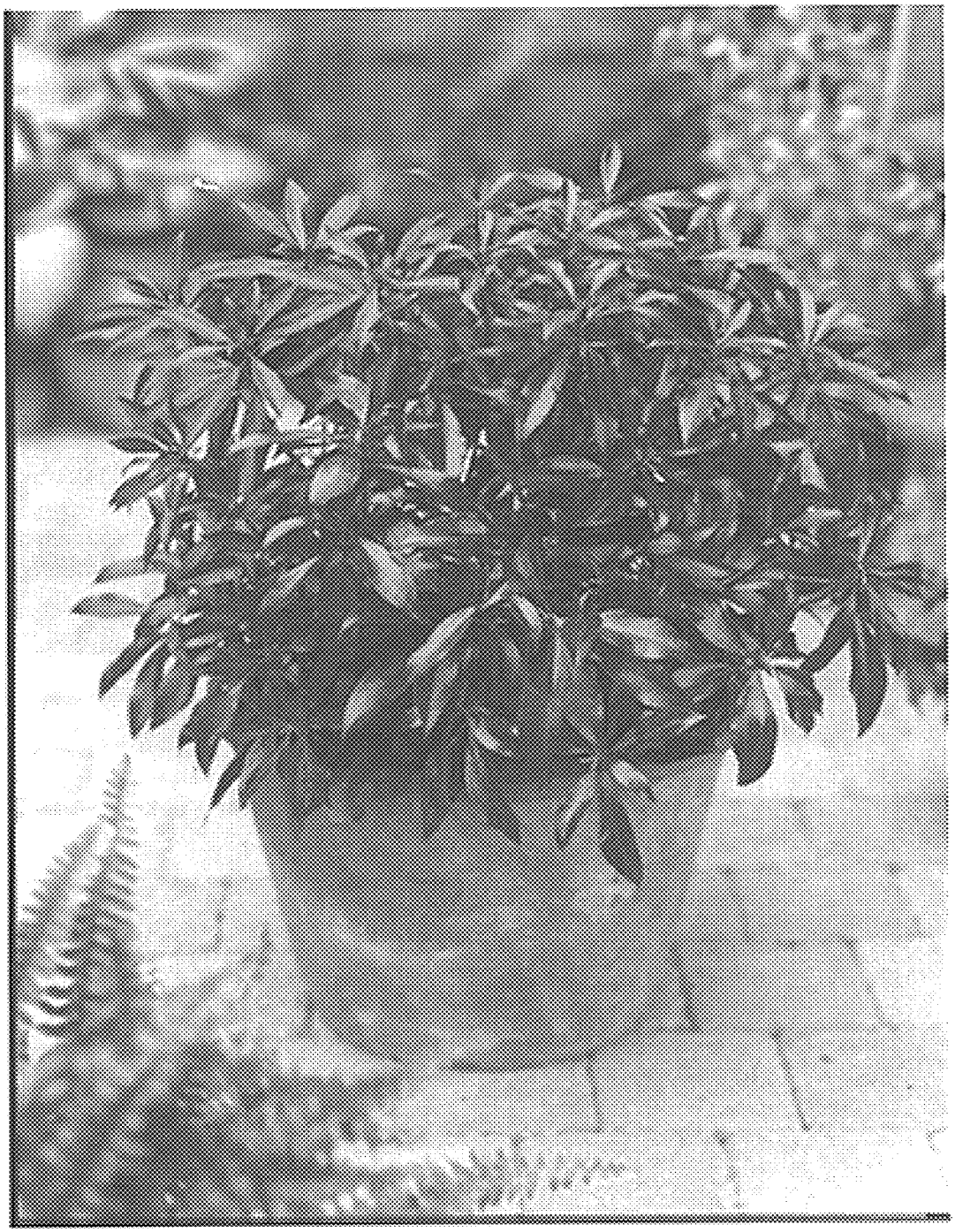

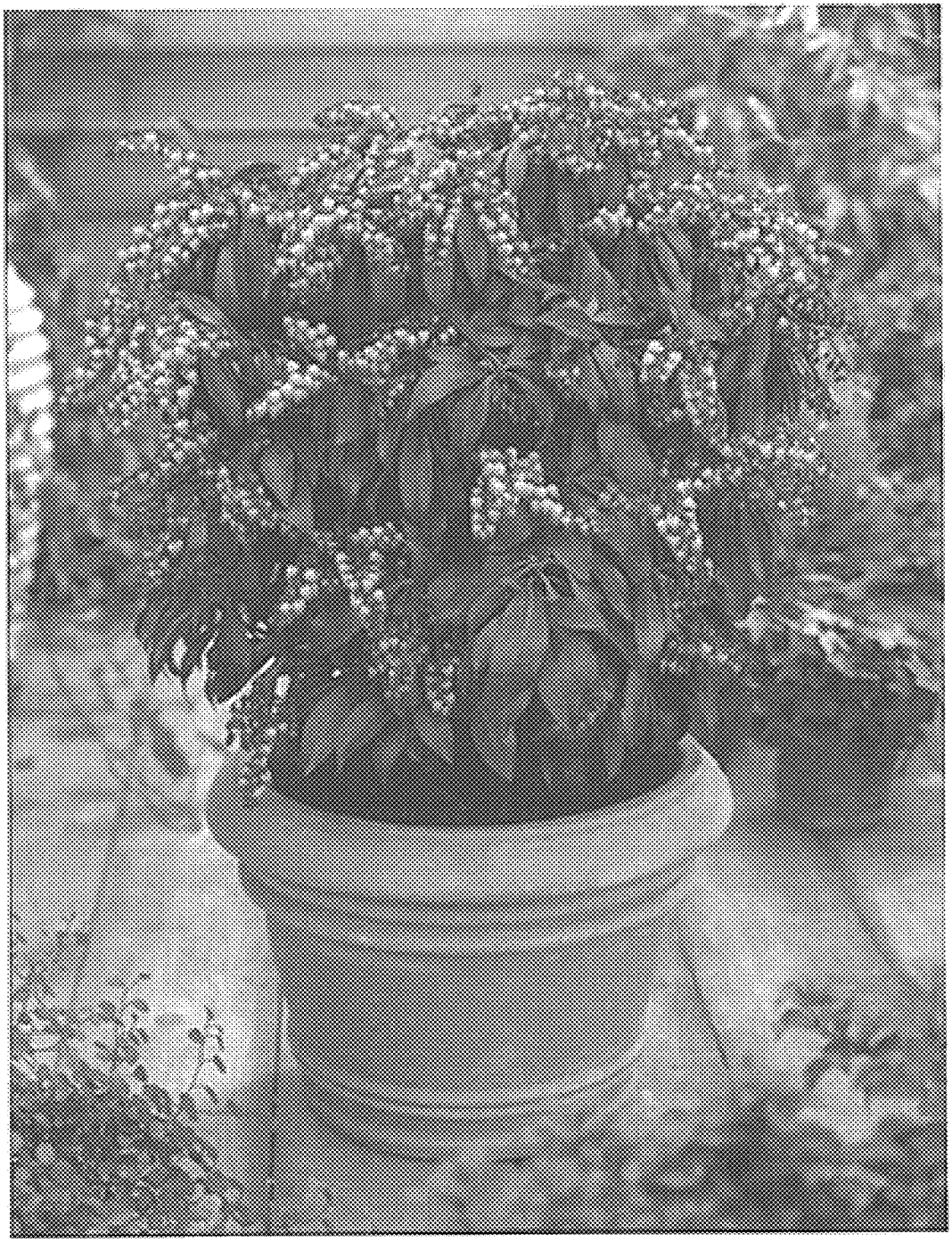

* * * * *